(12) United States Patent
Termanini

(10) Patent No.: US 9,119,724 B2
(45) Date of Patent: *Sep. 1, 2015

(54) INTERLOCKING REVERSE HIP REVISION PROSTHESIS

(71) Applicant: Hip Innovation Technology LLC, Plantation, FL (US)

(72) Inventor: Zafer Termanini, Boca Raton, FL (US)

(73) Assignee: Hip Innovation Technology LLC, Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/973,291

(22) Filed: Aug. 22, 2013

(65) Prior Publication Data

US 2013/0345823 A1    Dec. 26, 2013

Related U.S. Application Data

(63) Continuation-in-part of application No. 13/024,381, filed on Feb. 10, 2011, now Pat. No. 8,540,779, which is a continuation-in-part of application No. 12/799,609, filed on Apr. 28, 2010, now Pat. No. 8,313,531.

(60) Provisional application No. 61/339,680, filed on Mar. 8, 2010.

(51) Int. Cl.
*A61F 2/34* (2006.01)
*A61F 2/36* (2006.01)
(Continued)

(52) U.S. Cl.
CPC ... *A61F 2/40* (2013.01); *A61F 2/32* (2013.01); *A61F 2/34* (2013.01); *A61F 2/3609* (2013.01);
(Continued)

(58) Field of Classification Search
CPC ............ A61F 2002/30332; A61F 2002/30518; A61F 2002/30649; A61F 2002/3065; A61F 2002/30654; A61F 2/32; A61F 2/34; A61F 2002/3483; A61F 2/3607; A61F 2002/3615; A61F 2/40; A61F 2002/4085

USPC ............... 623/19.11–19.14, 22.11–22.14, 623/22.4–22.46, 23.11–23.14, 23.39–23.43, 623/908

See application file for complete search history.

(56) References Cited

U.S. PATENT DOCUMENTS 3,506,982 A    4/1970  Steffee
3,837,008 A    9/1974  Bahler et al.
(Continued)

FOREIGN PATENT DOCUMENTS

EP    0 322 493 B1    8/1991
EP    1 508 315 A2    2/2005
(Continued)

OTHER PUBLICATIONS

International Search Report dated May 9, 2011 from US International Searching Authority.
(Continued)

*Primary Examiner* — Marcia Watkins
(74) *Attorney, Agent, or Firm* — Norris McLaughlin & Marcus PA

(57) ABSTRACT

A reverse hip prosthesis comprising an acetabular cup for implanting in a previously implanted acetabular cup. The acetabular cup is secured to the previously implanted acetabular cup using an o-ring. The acetabular cup has a stem extending from the center of a concave portion thereof and an acetabular ball is attached to the stem, preferably by means of a Morse taper. A femoral implant is provided with a femoral cup attached to the proximal end thereof. The femoral cup has a stem which can be constructed in a modular fashion with several stem lengths in order to accommodate the various sizing requirements of different patients. After implantation of the acetabular cup and ball and the femoral cup, the members are assembled together so that the femoral cup can articulate on the acetabular ball. As the femoral cup is articulated, the edge of the femoral cup moves into a space located between the acetabular cup and the acetabular ball and thereby becomes constrained, thus reducing the likelihood of dislocation during extreme ranges of motion.

10 Claims, 9 Drawing Sheets

(51) Int. Cl.
*A61F 2/40* (2006.01)
*A61F 2/32* (2006.01)
*A61F 2/30* (2006.01)

(52) U.S. Cl.
CPC ....... *A61F 2/3607* (2013.01); *A61F 2002/3069* (2013.01); *A61F 2002/30247* (2013.01); *A61F 2002/30332* (2013.01); *A61F 2002/30614* (2013.01); *A61F 2002/30616* (2013.01); *A61F 2002/30649* (2013.01); *A61F 2002/30784* (2013.01); *A61F 2002/3401* (2013.01); *A61F 2002/3483* (2013.01); *A61F 2002/3615* (2013.01); *A61F 2002/4011* (2013.01); *A61F 2002/4022* (2013.01); *A61F 2002/4033* (2013.01); *A61F 2002/4085* (2013.01); *Y10S 623/908* (2013.01)

(56) References Cited

U.S. PATENT DOCUMENTS

| | | | |
|---|---|---|---|
| 3,868,730 | A | 3/1975 | Kaufer et al. |
| 3,916,451 | A | 11/1975 | Buechel et al. |
| 3,978,528 | A | 9/1976 | Crep |
| 4,030,143 | A | 6/1977 | Elloy et al. |
| 4,206,517 | A | 6/1980 | Pappas et al. |
| 4,693,723 | A | 9/1987 | Gabard |
| 4,792,337 | A | 12/1988 | Müller |
| 4,846,840 | A | 7/1989 | Leclercq et al. |
| 5,092,898 | A | 3/1992 | Bekki et al. |
| 5,462,563 | A | 10/1995 | Shearer et al. |
| 6,010,535 | A | 1/2000 | Shah |
| 6,527,808 | B1 | 3/2003 | Albertorio et al. |
| 6,749,637 | B1 | 6/2004 | Bäehler |
| 6,790,234 | B1 | 9/2004 | Frankle |
| 6,800,095 | B1 | 10/2004 | Pope et al. |
| 7,011,686 | B2 | 3/2006 | Ball et al. |
| 7,033,396 | B2 | 4/2006 | Tornier |
| 7,169,184 | B2 | 1/2007 | Pria |
| 7,175,663 | B1 | 2/2007 | Stone |
| 7,241,314 | B1 | 7/2007 | Winslow |
| 7,309,360 | B2 | 12/2007 | Tornier et al. |
| 7,462,197 | B2 | 12/2008 | Tornier et al. |
| 7,465,319 | B2 | 12/2008 | Tornier |
| 7,470,287 | B2 | 12/2008 | Tornier |
| 7,611,539 | B2 | 11/2009 | Bouttens et al. |
| 7,854,768 | B2 | 12/2010 | Wiley et al. |
| 8,313,531 | B2* | 11/2012 | Termanini ............ 623/22.15 |
| 8,540,779 | B2* | 9/2013 | Termanini ............ 623/22.15 |
| 8,747,481 | B2* | 6/2014 | Maurer ................ 623/22.11 |
| 8,920,510 | B2 | 12/2014 | Forsell |
| 2002/0143402 | A1 | 10/2002 | Steinberg |
| 2002/0173853 | A1 | 11/2002 | Corl, III et al. |
| 2003/0114934 | A1 | 6/2003 | Steinberg |
| 2003/0120347 | A1 | 6/2003 | Steinberg |
| 2004/0039449 | A1 | 2/2004 | Tornier |
| 2004/0220673 | A1 | 11/2004 | Pria |
| 2005/0165490 | A1 | 7/2005 | Tornier |
| 2005/0288791 | A1 | 12/2005 | Tornier et al. |
| 2006/0069443 | A1 | 3/2006 | Deffenbaugh et al. |
| 2007/0156246 | A1 | 7/2007 | Meswania et al. |
| 2008/0154369 | A1* | 6/2008 | Barr et al. ............ 623/11.11 |
| 2009/0112328 | A1 | 4/2009 | Tornier et al. |
| 2009/0113238 | A1 | 4/2009 | Liu et al. |
| 2009/0192621 | A1 | 7/2009 | Winslow |
| 2009/0287309 | A1 | 11/2009 | Walch et al. |
| 2010/0131073 | A1 | 5/2010 | Meridew et al. |
| 2010/0222886 | A1 | 9/2010 | Wiley et al. |
| 2011/0054628 | A1 | 3/2011 | Banks et al. |
| 2011/0151259 | A1 | 6/2011 | Jarman-Smith et al. |
| 2011/0218637 | A1 | 9/2011 | Termanini |
| 2011/0218638 | A1 | 9/2011 | Termanini |
| 2011/0218645 | A1 | 9/2011 | Garcia Saban et al. |
| 2011/0230590 | A1 | 9/2011 | Jarman-Smith et al. |
| 2012/0116533 | A1 | 5/2012 | Forsell |
| 2013/0345823 | A1* | 12/2013 | Termanini ............ 623/22.16 |
| 2014/0128982 | A1* | 5/2014 | Termanini ............ 623/19.13 |
| 2014/0156011 | A1* | 6/2014 | Termanini ............ 623/19.12 |

FOREIGN PATENT DOCUMENTS

| | | |
|---|---|---|
| EP | 1 543 801 B1 | 8/2007 |
| FR | 2603476 A1 | 3/1988 |
| FR | 2841768 A1 | 1/2004 |
| JP | 1175846 A | 7/1989 |
| JP | 200473854 A | 3/2004 |
| JP | 2005177496 A | 7/2005 |
| JP | 2005-538778 A | 12/2005 |
| TW | 2011/12996 A1 | 4/2011 |
| WO | WO9710776 A3 | 3/1997 |
| WO | WO2011/006852 A1 | 1/2001 |
| WO | WO2011/005214 A1 | 7/2010 |

OTHER PUBLICATIONS

Communication from EPO dated Apr. 18, 2013 and Supplementary European Search Report dated Apr. 9, 2013.

A. Roth, K. Sander, F. Layher, J. Babisch, R. Venbrocks; "In vivo measurement of polyethylene wear in cementless total hip arthroplasty"; Acta Chir Orthop Traumatol Cech. Feb. 2010;77(1):13-7; Clinic of Orthopaedics, Rudolf-Elle Hospital, Department of Orthopoaedics of the Friedrich-Schiller University of Jena, Eisenberg, Germany; ajroth@gmx.de.

G. Schmidig, A. Patel, I. Kiepins, M. Thakore, DC Markel; "The effects of acetabular shell deformation and liner thickness on frictional torque in ultrahigh-molecular-weight polyethylene acetabular bearings"; J. Arthroplasty, Jun. 2010; 25(4):644-53. Epub Jun. 2, 2009; Stryker Orthopaedics, Mahway, New Jersey, USA.

H. Ito, A. Minami T. Matsuno, H. Tanino, T. Yuhta, I. Nishimura; "The sphericity of the bearing surface in total hip arthroplasty", J. Arthroplasty, Dec. 2001;16(8):1024-9; Department of Orthopaedic Surgery, Hokkaido University, School of Medicine, Sapporo, Japan; itobiro@med.hokudai.ac.jp.

P. Hernigou, T. Bahrami; "Zirconia and alumina ceramics in comparison with stainless-steel heads. Polyethylene wear after a minimum ten-year follow-up"; J Bone Joint Surg. Br. May 2003;85(4):504-9.

D. Dowson, ZM Jin; Metal-on-metal hip joint tribology; Proc Inst Mech Eng H. Feb. 2006;220(2);107-18.

Chen, Cheng-Fong; Chen, Wei-Ming; Yang, Chan-Tsung; Huang,Ching-Kuei; Chen, Tain-Hsiung; Hybrid Assembly of Metal Head and Femoral Stem from Manufacturers During Isolated Acetabular Revision; Artificial Organs, vol. 34, Issue 8, pp. E242-E245; Publ. Aug. 2010.

Beldame, J.; Carreras, F.; Oger, P.; Beaufils, P.; Cementless cups do not increase osteolysis risk in metal-on-metal total hip arthroplasty; Orthopaedics & Traumatology-Surger & Research, vol. 95, Issue 7, pp. 478-490, Publ. Nov. 2009, Elsevier Masson SAS.

Pavelka, T; Linhart, M; Houcek, P.; [Hip joint arthroplasty following surgical treatment of acetabular fracture]—Aloplastika kycelniho kloubu po operacnim leceni zlomenin acetabula; Acta chirurgiae orthopaedicae et traumatologiae Cechoslovaca, vol. 73, Issue 4, pp. 268-274; Publ. Aug. 2006.

Hamadouche, M; Madi, F.; Kerboull, L.; Courpied, Jr.; Kerboull, M.; Early femoral osteolysis following Charnley-Kerboull total hip arthroplsty combining a 22-mm zirconia head on polyethylene; Revue De Chirurgie Orthopedique et Reparatrice de l Appareil Moteur, vol. 91, Issue 5, pp. 439-445, Publ. Sep. 2005, Elsevier SAS.

Bal, BS; Vandelune, D.; Gurba, DM; Jasty, M.; Harris, WH; Polyethylene wear in cases using femoral stems of similar geometry, but different metals, porous layer, and modularity; Journal of Arthroplasty, vol. 13, Issue 5, pp. 492-499; Publ. Aug. 1998.

Schreurs, B. Willem; Van Tienen, Tony G.; Buma, Pieter; Verdonschot, Nico; Gardeniers, Jean WM; Sloofe Tom JJH; Favorable results of acetabular reconstruction with impacted morsellized bone grafts in patients younger than 50 years: A 10- to 18-year follow-up study of 34 cemented total hip arthroplasties; Journal: Acta orthopaedica Scandinavica, 72 (2), 120-126; Publ. 2001, INST-CNRS.

* cited by examiner

INTERLOCKING REVERSE HIP REVISION PROSTHESIS

CROSS REFERENCE TO RELATED APPLICATION

This application is a continuation-in-part of U.S. patent application Ser. No. 13/024,381 filed Feb. 10, 2011 which is a continuation-in-part of U.S. Pat. No. 8,313,531 B2 which claimed the benefit of U.S. Provisional Patent Application Ser. No. 61/339,680 filed on Mar. 8, 2010 and entitled "INTERLOCKING REVERSE HIP PROSTHESIS" and the entirety of the foregoing applications and patent are incorporated herein by reference.

BACKGROUND OF THE INVENTION

1. Field of the Invention

The present invention relates generally to hip prostheses and more specifically to an interlocking reverse hip prosthesis allowing increased range of motion and stability during excessive range of motion.

2. Description of the Prior Art

It can be appreciated that several hip implants have been in use for years. Typically, conventional hip implants comprise a femoral component having an articular femoral ball attached to a stem. A femoral stem is inserted into the medullary canal of the femur after preparation and reaming using appropriate reamers by the operating surgeon. The stem can be secured with bone cement or press fit. An acetabular component having the shape of a cup is inserted into an acetabular socket after preparation and appropriate reaming and secured with cancellous screws through holes in the cup. It can also be secured with bone cement or press fit or a combination thereof.

The acetabular cup is metallic and it is internally lined with high-density polyethylene or ceramic. Said lining is secured into the acetabular cup by a press-fit mechanism.

The main problem with conventional hip implants is the instability of the prosthesis at the extreme range of motion, thereby allowing the articular femoral ball to dislodge and dislocate. Prior art teaches constrained and preassembled ball and cup devices or devices wherein the ball and cup members are implanted separately whereupon the ball element is forced into a resilient opening in the cup and thereafter held in place by the resilient material. Other constrained acetabular cups may include a locking ring such as the one described by Albertorio et al. U.S. Pat. No. 6,527,808. In the case of cup elements having retaining rings, the ball member is forcefully inserted into the cup after the two elements are implanted. This constitutes a weak link where forces exerted on the prosthesis by ambulatory motion may exceed the forces used to assemble the implant thereby causing the ball to be separated from the cup.

While these devices may be suitable for the particular purpose which they address, they do not provide an interlocking mechanism as in the reverse hip implant design of the present invention. The very nature of applicant's design allows increased range of motion and increased stability at extreme ranges of motion thereby reducing the risk of dislocation.

In these respects, the interlocking reverse hip prosthesis according to the present invention substantially departs from the conventional concepts and designs of the prior art because the articular femoral ball of the prior art is replaced with an articular femoral cup and the acetabular cup is provided with an acetabular ball. Thus an apparatus is provided which is primarily developed for the purpose of reducing the risk of dislocation of hip implants at extreme ranges of motion.

Furthermore, since the articular surface of the femoral cup of the invention is fully in contact 100% of the time with the surface of the acetabular ball, it is clear that this will improve tribology because the weight bearing distribution is improved on the articular surfaces, thus decreasing the wear of the surfaces in contact and reducing the risk of wear particles being released in the joint. The later, being very detrimental to the proper function of the joint.

SUMMARY OF THE INVENTION

The present invention provides a new interlocking reverse hip prosthesis construction wherein an acetabular ball is solidly and concentrically attached to a central protrusion or stem of the acetabular cup via Morse taper. A metallic acetabular cup is used in the preferred embodiment. A femoral cup, also referred to herein as a hemispherical femoral cup or an articular femoral cup, is preferably solidly attached to a femoral implant by means of a Morse taper. Other means of attachment known to those in the art can be used. And whenever a Morse taper is referred to herein, it is intended to describe a preferred embodiment. The Morse taper can be replaced by other suitable means of attachment as will be apparent to those having skill in the art.

The acetabular cup is implanted in an acetabular socket constructed by the surgeon in the pelvic bone to which it is firmly secured by one or more fasteners through one or more openings in the acetabular cup. The fasteners can be cancellous screws or biocompatible resorbable studs of variable number. The femoral implant is then inserted and impacted into the femoral medullary canal which has been prepared and hollowed by the surgeon using appropriate reamers. During ambulation, the articular femoral cup edge or lip will glide conformably and concentrically into a space located between the acetabular ball and the acetabular cup. As will be apparent to those having skill in the art, the geometrical configuration of applicant's invention makes it very difficult for the femoral cup to dislocate when the range of motion increases since it becomes constrained in the locking space between the acetabular cup and the acetabular ball.

As noted above, the articular surface of the femoral cup is fully in contact at all times with the articular surface of the acetabular ball. This improves the weight distribution, decreases the wear of the surfaces in contact and reduces the risk of wear particles being released in the joint.

In an optional embodiment of the invention, applicant has addressed the rare possibility that soft tissue may get lodged in the implant in the space between the acetabular cup and the acetabular ball. A protective sheath can be used to avoid this possibility. As discussed in more detail below, the sheath is disposed in the space between the acetabular cup and the acetabular ball and is allowed to glide freely therein.

There has thus been outlined the more important features of the invention in order that the detailed description may be better understood, and so that the present contribution to the art may be better appreciated. A novel feature of this invention is that the location of the articular surfaces of the hip joint, namely the ball and socket, is reversed. This results in a new reverse hip implant which is not anticipated, rendered obvious, suggested or even implied by any prior hip prosthesis when considered alone or in any combination.

In this respect, before explaining at least one embodiment of the invention in detail, it is to be understood that the invention is not committed in its application to the details of construction and arrangements of the components set forth in the following description or illustrated in the drawings. The invention is capable of other embodiments and of being practiced and carried out in various ways as will be apparent from the description herein to those having skill in the art. Also, it is to be understood that the terminology employed herein are for the purpose of the description and should not be regarded as limiting. Moreover, the term "hemispherical" as it is used herein means "having the shape of a portion of a sphere" and it is not limited to one-half of a sphere but may be less than one-half of a sphere or more than one-half of a sphere as will be apparent to those having skill in the art consistent with functionality.

To the accomplishment of the above and related objects, this invention may be embodied in the form illustrated in the accompanying drawings. However, the drawings are elicited only and changes may be made into any specific construction illustrated without departing from the principles of the invention.

BRIEF DESCRIPTION OF THE DRAWINGS

Various other objects, features and advantages of the present invention will become fully appreciated as the same becomes better understood when considered in conjunction with the accompanying drawings, in which like reference characters designate the same or similar elements throughout the several views, and wherein.

DETAILED DESCRIPTION OF THE INVENTION

Figure 1:
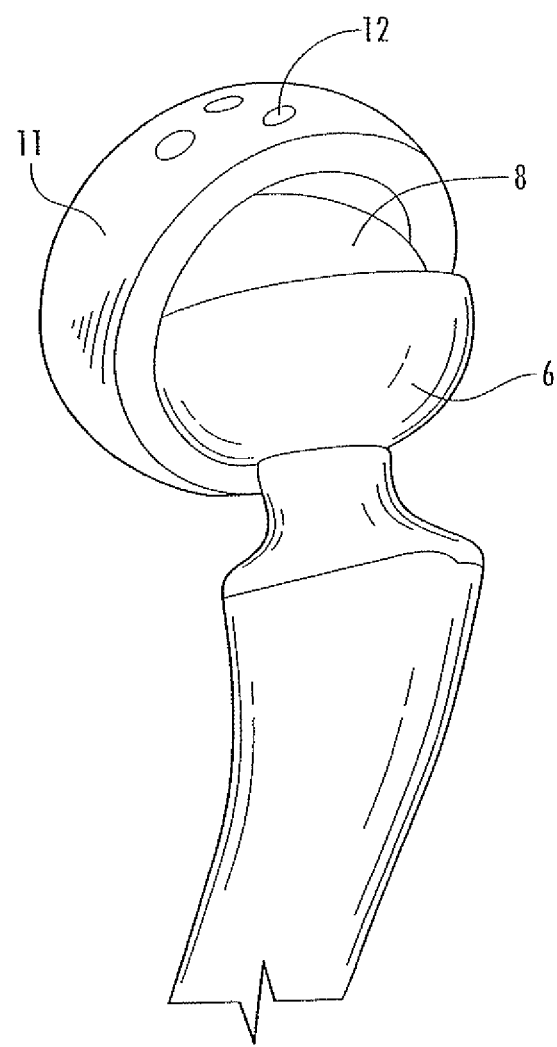
FIG. 1 is a perspective view of the interlocking reverse hip prosthesis of the invention.

Turning now to the drawings, in which the reference characters denote the same or similar elements throughout the several views, FIGS. 1-4 illustrate an interlocking reverse hip prosthesis, which comprises an acetabular cup (11) having a smooth concave surface and a convex nonarticular surface. The convex non-articular surface abuts a socket in the pelvic bone when the acetabular cup is implanted in a patient and provides a porous surface with multiple asperities and microvoids to allow bone ingrowth. Furthermore, the acetabular cup (11) provides one or more holes (12) at different locations for the purpose of using one or more fasteners (14). The fasteners (14) can be screws or resorbable nonmetallic and biocompatible studs of different diameters and lengths. The studs, which can be called orthobiologic resorbable studs, will secure the acetabular cup (11) during the initial phase of bone ingrowth and will resorb within one year, being replaced by newly generated bone and become part of the host pelvic bone. During that period, the acetabular cup (11) becomes solidly attached to the acetabular socket in the pelvic bone (4) by bone ingrowth. The acetabular cup (11) has a concave hemispherical surface in which a large acetabular cup stem (9) is disposed. The acetabular cup stem (9) has a male Morse taper for assembly to the acetabular ball (8) by means of the acetabular ball recess (10) which has a female Morse taper. Referring to FIGS. 2-4 and 6, the femoral cup (6) has a femoral cup stem (7) with a male Morse taper while the femoral implant (1) has a cooperating femoral implant recess (5) having a female Morse taper located in neck (3). FIGS. 7 and 8 illustrate a femoral cup (20) with a neck (22) and a femoral cup recess (21) having a female Morse taper. This cooperates with a femoral implant stem having a male Morse taper (not shown). In a preferred embodiment, a modular system is used in a kit according to the invention wherein the femoral cup stem (7) or neck (22) can come in different lengths to accommodate the sizing needs of a patient. Therefore, in a kit of the invention, two or more femoral cups are provided having different stem lengths. In a less preferred embodiment, the length of the neck (3) of femoral implant (1), or the femoral implant stem (not shown) can also have various lengths to accommodate patient sizing needs and in a kit comprising this embodiment two or more neck or stem components having different lengths will be included. Other variations on the design to meet different sizing needs will be apparent to those having skill in the art.

An important advantage of the present invention is that the greater the interdigitation the more stability of the implant as opposed to conventional ball and socket hip implants, where increased range of motion is usually associated with increased risk of dislocation.

Figure 2:
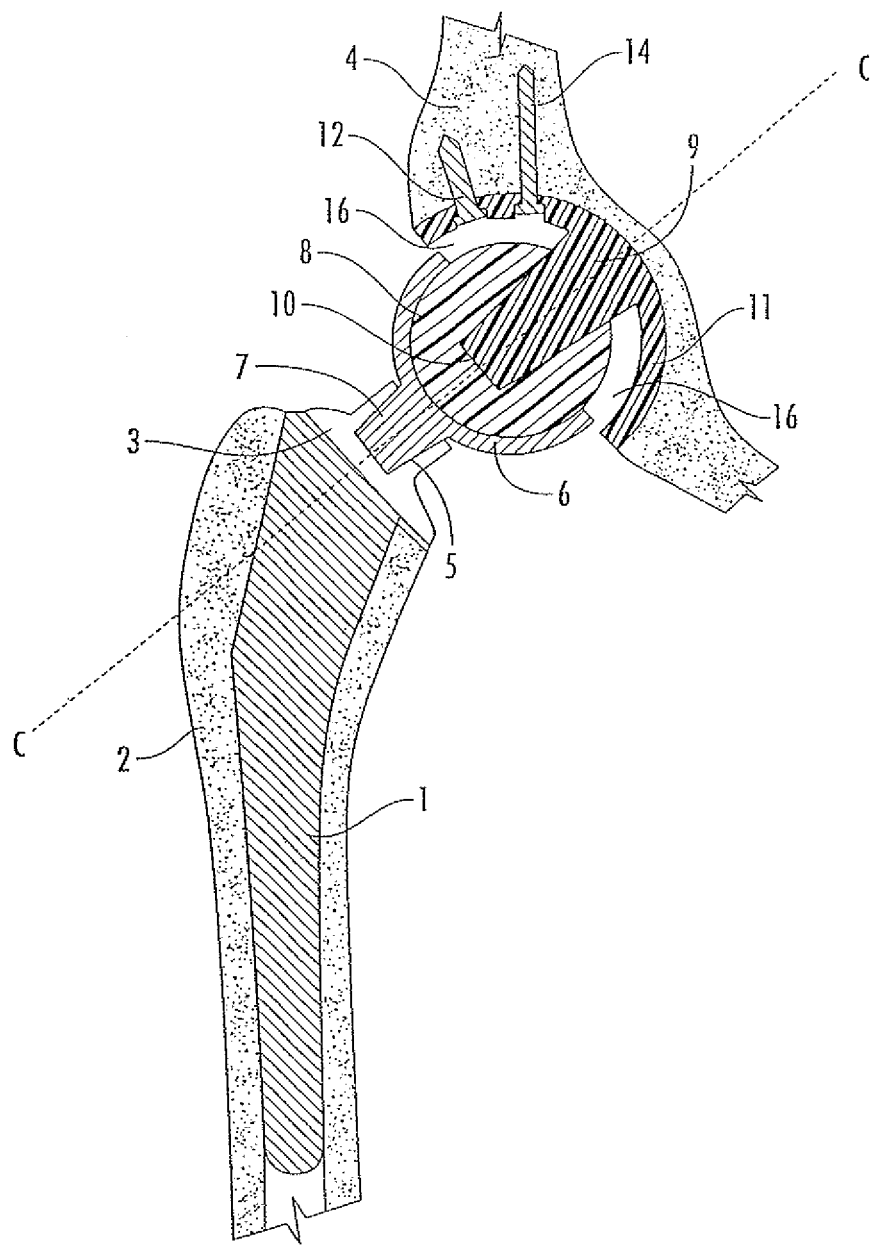
FIG. 2 is a section view of the interlocking reverse hip prosthesis.

Referring to FIG. 2, the proximal femoral bone (2) is reamed in the usual fashion to accept a femoral implant (1) that can be cemented or press fitted in the femoral medullary canal. The acetabular socket in the pelvic bone (4) is reamed to the appropriate size to accept the acetabular cup (11), which is impacted for press fit at the correct angle of inclination and anteversion. Fasteners (14) in the form of fixation screws or biocompatible resorbable studs are then inserted in place to secure the acetabular cup (11). The acetabular ball (8) is then affixed onto the acetabular cup stem (9). FIG. 2 also illustrates center line (C-C). In the position shown, the center line (C-C) passes through the center of the acetabular cup (11), the longitudinal center line of the acetabular cup stem (9), the center of acetabular ball (8), the longitudinal center line of femoral cup stem (7) and the longitudinal center line of femoral implant recess (5). Obviously, when the femoral cup is articulated on the ball the center line associated with the femoral components will not be colinear with the center line of the acetabular components. The line is simply illustrated in this way for convenience.

Figure 3:
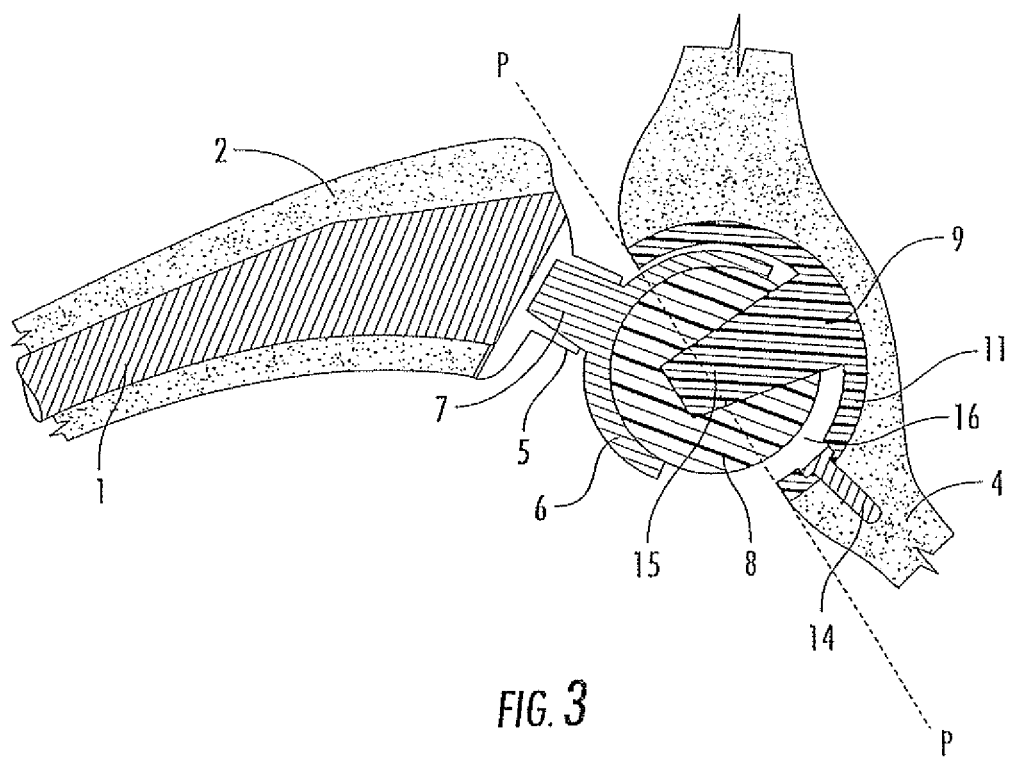
FIG. 3 is a section view of the interlocking reverse hip prosthesis in extension and external rotation.
Figure 4:
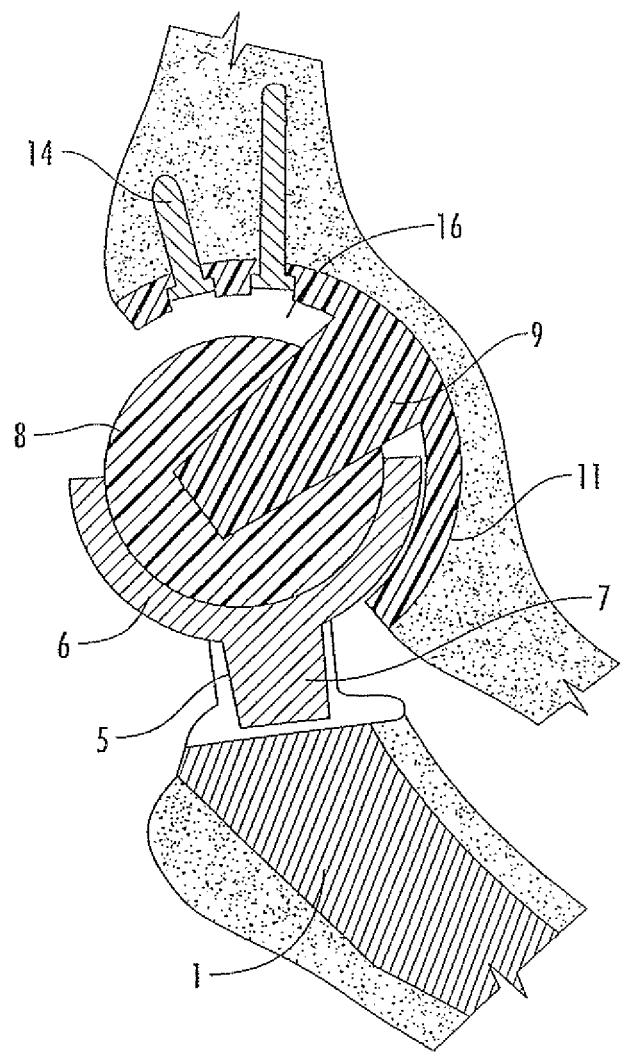
FIG. 4 is a section view of the interlocking reverse hip prosthesis in flexion and internal rotation.

Referring to FIGS. 3, 4 and 8, when the femoral cup (6) or (20) articulates on the acetabular ball (8), the edges of the femoral cup (6) or (20) move into and out of hemispherical space (16) and the articular surface of the femoral cup (6) or (20) maintains the same area of contact with the acetabular ball (8) over the entire range of motion. In other words, 100% of the articular contact area of the femoral cup (6) or (20) is maintained over the entire range of motion. FIG. 3 illustrates the prosthesis of the invention in extension and external rotation. FIG. 4 illustrates the prosthesis in flexion and internal rotation and FIG. 8 illustrates an extreme articulation position of the femoral cup (20) on the acetabular ball (8).

In one embodiment, the articular surface of the femoral cup (6) or (20) contains a high molecular weight polyethylene lining of varying thickness, but no less than 4 mm. In a different embodiment the lining could be porcelain, ceramic or a metallic alloy.

An important feature of the present invention is the ability to place acetabular ball (8) in a position that minimizes or eliminates tortional forces on the acetabular cup and acetabular stem. This is illustrated in FIG. 3 wherein the acetabular ball (8) is affixed on acetabular cup stem (9) in a position wherein the equatorial plane (P-P) of the acetabular cup passes through the center (15) of the acetabular ball.

Figure 5:
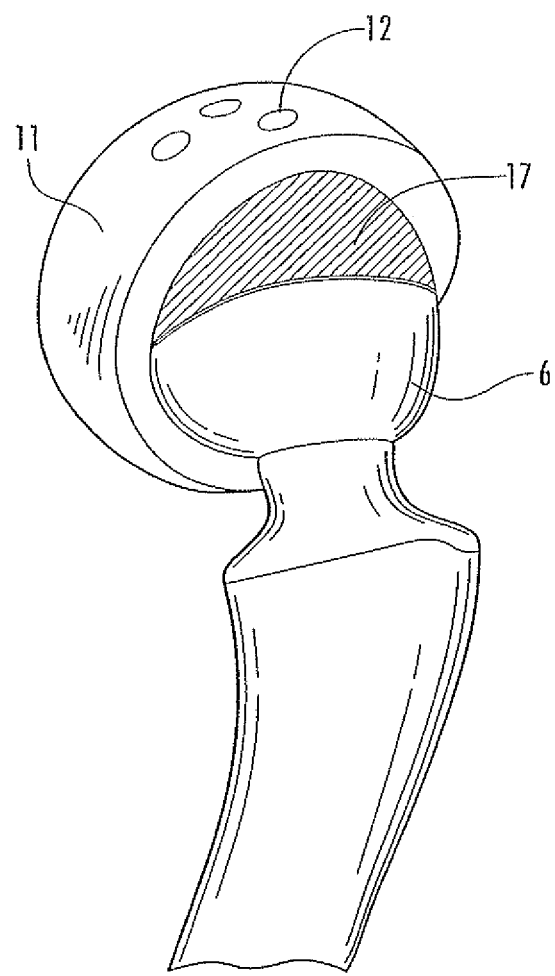
FIG. 5 is a perspective view of the prosthesis of the invention illustrating an optional soft tissue protective sheath.
Figure 5A:
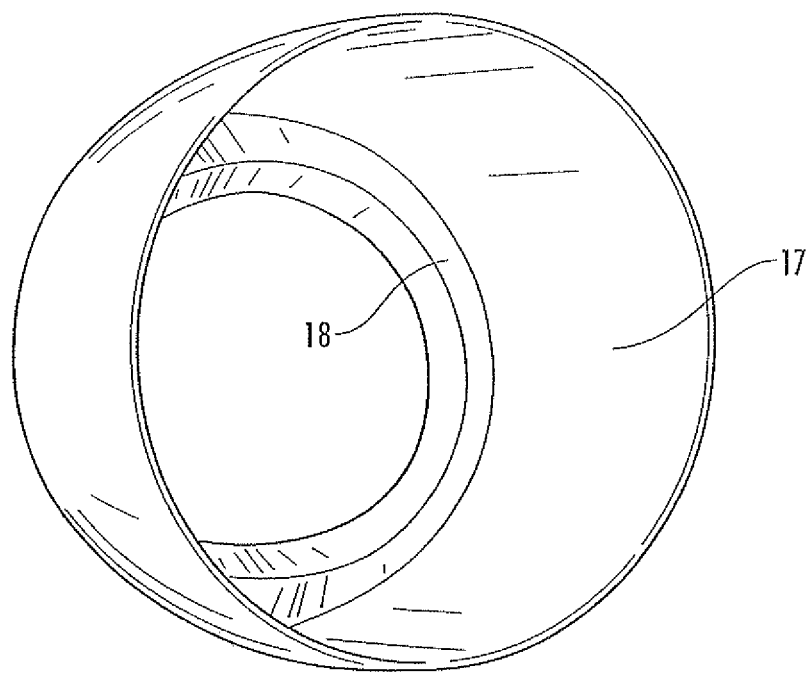
FIG. 5A is a perspective view of the protective sheath by itself.

An optional embodiment of the invention illustrated in FIGS. 5-8 adds a soft tissue protective sheath (17) to the embodiments described above. The protective sheath, also illustrated by itself in perspective in FIG. 5A, addresses the rare cases wherein soft tissue might get lodged in the space (16) as a result of articulation of the prosthetic joint of the invention.

Figure 6:
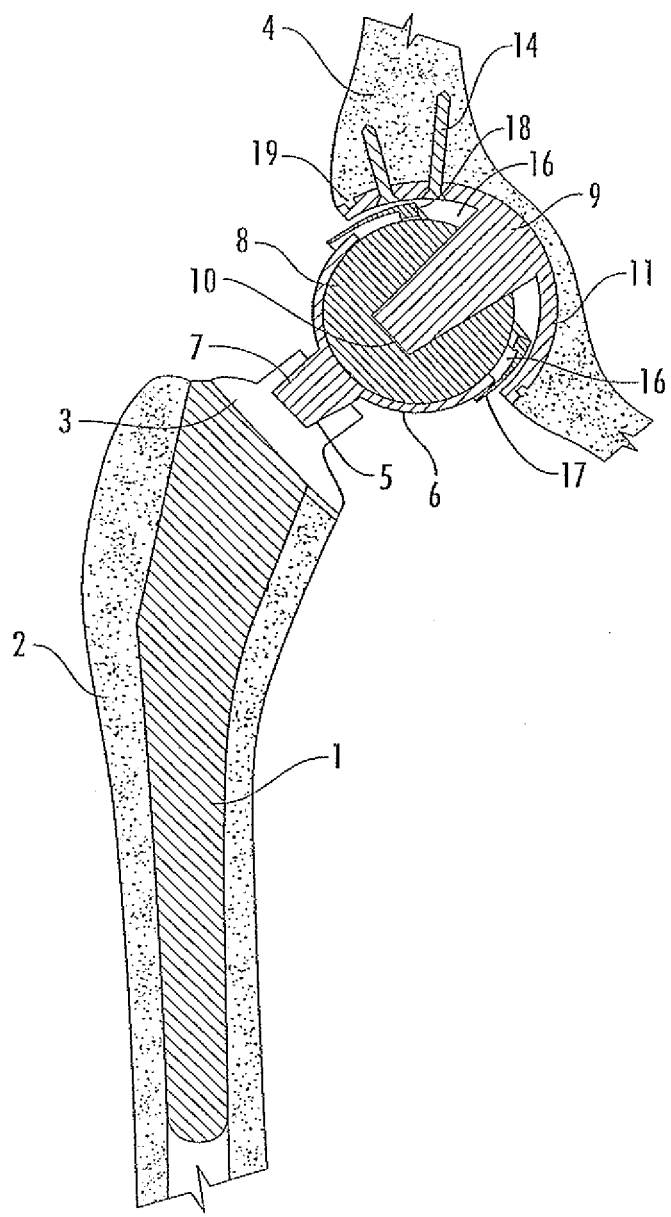
FIG. 6 is a section view of the embodiment of FIG. 5.
Figure 7:
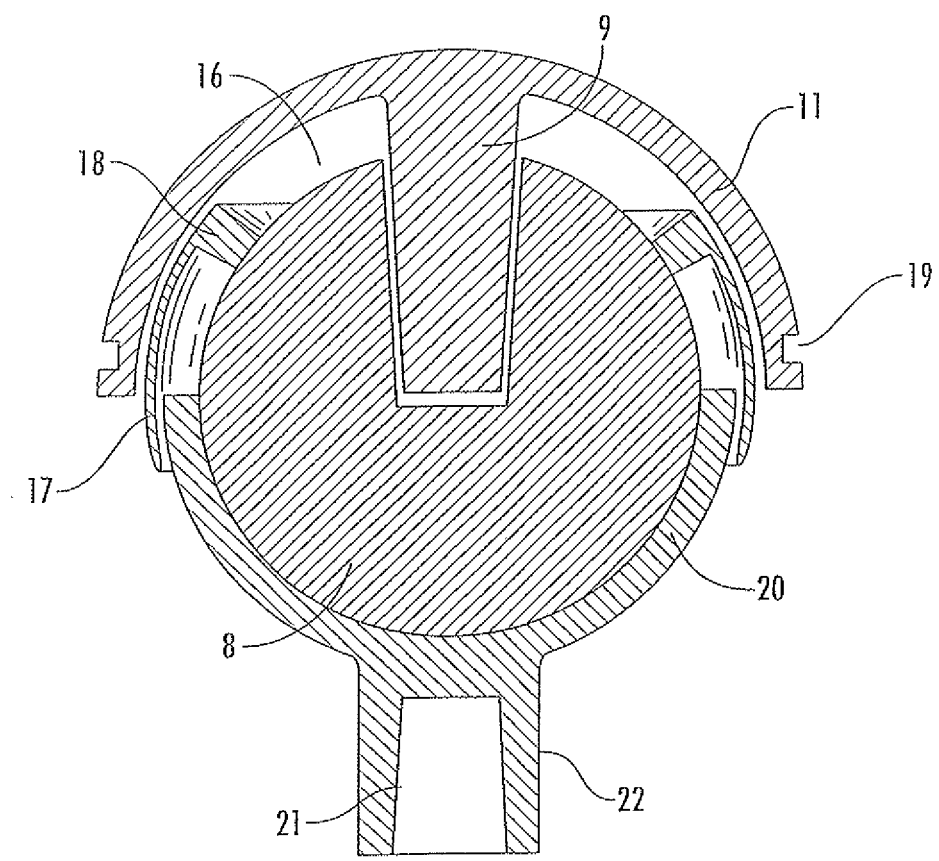
FIG. 7 is a section view illustrating a femoral cup having a recess instead of a stem for connection to a femoral implant.
Figure 8:
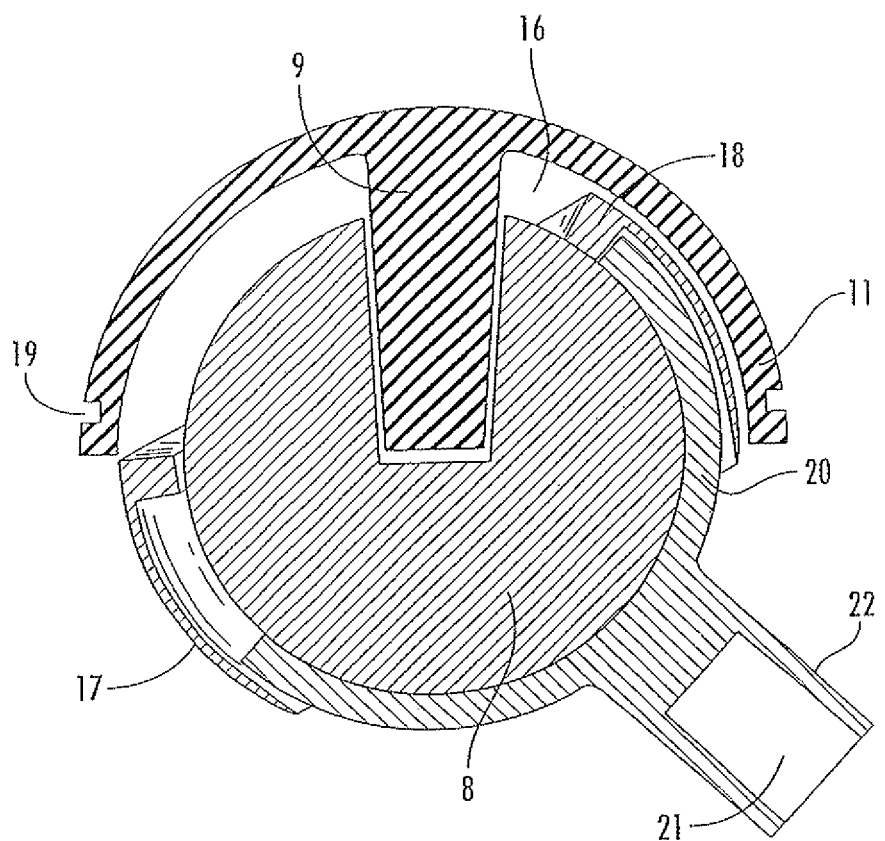
FIG. 8 is a section view of the embodiment of FIG. 7 which has been articulated to an extreme position.

Referring to FIGS. 6-8, the sheath (17) extends beyond the circular outer edge of the acetabular cup (11) and has a retaining ring (18). The sheath (17) is installed by placing it into the acetabular cup (11) before the acetabular ball (8) is installed. The sheath (17) can have a solid surface as illustrated or it can be perforated with holes, slots or the like having the same or different shapes and dimensions as may be desired.

As can be seen from FIGS. 6-8, the sheath (17) is allowed to move freely within the space (16), restrained only by the acetabular ball (8) and acetabular cup stem (9). The sheath (17) also is moved by contact of retaining ring (18) with the outer edge of femoral cup (6) or (20). The retaining ring (18) will, for example, contact the outer edge of femoral cup (6) or (20) particularly in positions of extreme articulation of the prosthetic joint as illustrated in FIG. 8.

In another embodiment of the present invention, also illustrated in FIGS. 6-8, the acetabular cup (11) is designed for use in revision surgery of the hip. Revisions are surgical procedures where the existing implant is removed. This most frequently requires removal of the acetabular cup and it is associated with a high level of morbidity. The removal of a previously implanted acetabular cup may be quite difficult surgically, especially when the cup has metallic beads for bone ingrowth. In these cases, the removal is also associated with iatrogenic bone loss leading to difficulty in inserting another conventional acetabular cup.

There are instances where the acetabular cup was not implanted correctly or where the lining of the existing implant becomes worn out and needs to be replaced. Recurrent dislocations of the hip implant are usually secondary to surgical misplacement of a conventional acetabular cup. For example, if during the initial procedure, the cup was placed either too vertical or retroverted (e.g., facing backward instead of forward).

To remedy the above cited complication, there are times where the surgeon simply cements a conventional revision cup into the previously implanted acetabular cup using conventional bone cement. However, problems arise if the initial position of the previously implanted acetabular cup is too vertical or retroverted, preventing a conventional revision cup from being glued in the previously implanted acetabular cup. As a result, removal of the previously implanted acetabular cup becomes necessary—entailing significant risk and possible morbidity to the patient as described above.

Another important advantage of the present invention is that the angle of inclination and retroversion are not critical since the interlocking mechanism of applicant's implant will compensate for the misalignment of a previously implanted acetabular cup.

Most previously implanted acetabular cups have an insert in a concave surface thereof. The insert provides a concave articulating surface for articulation of the femoral ball. The insert, also referred to herein as a removable articulating surface, can be made from a plastic, such as polyethylene, or any other suitable biocompatible material such as ceramic. The insert is frequently held in place by means of a circumferential groove, also referred to herein as a second circumferential groove, located in proximity to equatorial plane near the circumferential edge of the concave surface of the previously implanted acetabular cup. The circumferential groove may be engaged by a protrusion or protrusions extending from the insert, especially a flexible plastic insert, into the groove. Alternatively, an o-ring is snapped into the groove to hold the insert in place. Thus, it is removably affixed in the previously implanted acetabular cup by means of the second circumferential groove and a circumferential protrusion located in proximity to a circumferential edge on the outer or convex surface of the insert, or an o-ring, wherein the circumferential protrusion or o-ring is held in the second circumferential groove.

The acetabular cup (11) of applicant's interlocking reverse hip prosthesis can optionally be provided with a thin circumferential groove (19), also referred to herein as the first circumferential groove, located in proximity of the equatorial plane of said cup as illustrated in FIGS. 6-8.

In revision surgery using the hip prosthesis of applicant's invention, the insert of the previously implanted acetabular cup is removed. The circumferential groove (19) of the interlocking reverse hip prosthesis will host a retaining "o-ring" of the previously implanted acetabular cup being revised thereby providing solid fixation of applicant's revision interlocking reverse hip prosthesis to the previously implanted acetabular cup.

The revision surgery is performed by removing the removable articulating surface and then placing the o-ring in either the first circumferential groove or the second circumferential groove. Then the acetabular cup of the interlocking reverse hip prosthesis is pushed into the previously implanted acetabular cup until the o-ring snaps into place in both the first and second circumferential grooves, thereby solidly affixing the acetabular cup of the interlocking reverse hip prosthesis into the previously implanted acetabular cup.

The components of the reverse hip prosthesis of the invention are made from biocompatible materials commonly used in the art and suitable materials will be apparent to those skilled in the art based upon the disclosures herein. Metals or metallic alloys such as titanium or cobalt chrome are suitable. For some components, such as the acetabular ball, metals or ceramics can be used. High density polyethylene is also suitable for some components, for example the protective sheath or an optional lining for the concave portion of the femoral cup. Other biocompatible materials or combinations thereof can be used for various components as will be apparent to those having skill in the art.

The dimensions of the various components of the reverse hip prosthesis of the invention can be readily determined by those skilled in the art based upon the disclosures herein. For the acetabular cup, which is hemispherical, an outer diameter from about 35 millimeters (mm) to about 65 mm will be suitable for most applications. The spherical acetabular ball should have a diameter from about 28 mm to about 45 mm. The diameter of the acetabular ball should be from about 7 mm to about 12 mm smaller than the inner diameter of the acetabular cup, thus creating a hemispherical space or gap having a width from about 7 mm to about 12 mm to allow articulation of the femoral cup therein. Of course, the concave, hemispherical, articular surface of the femoral cup will be sized compatibly with the acetabular ball to allow for smooth articulation. Highly polished cobalt chrome is an excellent material for the articular surface of the femoral cup but other materials such as biocompatible metallic alloys can be used. The femoral cup also may contain a lining fabricated from high-density polyethylene, ceramic or biocompatible metallic alloys.

It is therefore the object of the present invention to provide a new and improved interlocking and restrained reverse hip prosthesis system, where two conventional articular surfaces of the hip joint are reversed and interlocked. The system described in the present invention, which has all of the advantages of the prior art designs, none of the disadvantages, and numerous improvements over the prior art, particularly in respect of remarkably increased range of motion and reduced risk of wear particles being released into the joint.

With respect to the above description then, it is to be realized that the optimum dimensional relationships for the parts of the invention, to include variations in size, materials, shape, form, function and manner of operation, assembly and use, are deemed readily apparent to those skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A hip prosthesis having increased stability at extreme ranges of motion comprising
    a unitary acetabular cup having a non-articulating surface for attachment to an acetabular socket in a pelvic bone and a concave surface located opposite to the non-articulating surface, the non-articulating surface having a circumferential groove adapted to receive an o-ring and located in proximity to a circumferential edge of the acetabular cup and the concave surface having an acetabular cup stem firmly affixed therein and projecting outwardly therefrom,
    an o-ring sized to fit in the circumferential groove,
    an acetabular ball firmly affixed to the acetabular cup stem, the acetabular ball having a surface,
    the concave surface of the acetabular cup and the surface of the acetabular ball are spaced from one another, thereby defining a gap therebetween,
    a femoral implant for implantation in a medullary canal of a proximal end of a femur, and
    a femoral cup firmly affixed to a proximal end of the femoral implant, the femoral cup being sized for articulation in the gap, such that the femoral cup has a concave surface sized for articulation on the surface of the acetabular ball and a convex surface opposite the concave surface of the femoral cup sized for articulation on the concave surface of the acetabular cup, the gap being sized and configured to permit said articulation while constraining the femoral cup within the gap throughout an entire range of said articulation of the femoral cup as it articulates within the gap, thereby reducing a risk of dislocation.

2. The prosthesis of claim 1 wherein the concave surface of the femoral cup is hemispherical and the concave surface of the acetabular cup is hemispherical.

3. The prosthesis of claim 1 wherein the concave surface of the acetabular cup has a center and the acetabular cup stem is affixed to and in the center.

4. The prosthesis of claim 1 wherein the acetabular ball has an acetabular ball recess sized to receive the acetabular cup stem.

5. The prosthesis of claim 4 wherein the acetabular ball has a center, the acetabular cup stem has a longitudinal center line and the acetabular ball recess has a longitudinal center line, both longitudinal center lines being colinear and passing through the center of the acetabular ball.

6. The prosthesis of claim 1 wherein the femoral cup has a femoral cup stem projecting outwardly therefrom in a direction opposite the concave surface thereof and the femoral implant has at its proximal end a recess sized to receive the femoral cup stem.

7. The prosthesis of claim 6 wherein the concave surface of the femoral cup is hemispherical and has a center line, the femoral cup stem has a longitudinal center line and the femoral implant recess has a longitudinal center line wherein all of the center lines are colinear.

8. The prosthesis of claim 1 wherein the femoral implant has a femoral implant stem extending proximally therefrom and the femoral cup has a recess sized to receive the femoral implant stem.

9. The prosthesis of claim 8 wherein the concave surface of the femoral cup is hemispherical and has a center line, the femoral implant stem has a longitudinal center line and the femoral cup recess has a longitudinal center line wherein all of the center lines are colinear.

10. The prosthesis of claim 1 wherein the concave surface of the femoral cup is fully in contact with the surface of the acetabular ball during articulation of said concave surface pan the acetabular ball.

\* \* \* \* \*